US011690964B2

(12) United States Patent
Longest et al.

(10) Patent No.: US 11,690,964 B2
(45) Date of Patent: Jul. 4, 2023

(54) DEVICES, SYSTEMS, AND METHODS FOR DRY POWDER THERAPIES

(71) Applicant: VIRGINA COMMONWEALTH UNIVERSITY, Richmond, VA (US)

(72) Inventors: Philip Worth Longest, Midlothian, VA (US); Michael Hindle, North Chesterfield, VA (US); Dale Farkas, Mechanicsville, VA (US); Susan Boc, Burlingame, CA (US)

(73) Assignee: Virginia Commonwealth University, Richmond, VA (US)

( * ) Notice: Subject to any disclaimer, the term of this patent is extended or adjusted under 35 U.S.C. 154(b) by 773 days.

(21) Appl. No.: 16/617,546

(22) PCT Filed: May 31, 2018

(86) PCT No.: PCT/US2018/035294
§ 371 (c)(1),
(2) Date: Nov. 27, 2019

(87) PCT Pub. No.: WO2018/222810
PCT Pub. Date: Dec. 6, 2018

(65) Prior Publication Data
US 2020/0139058 A1 May 7, 2020

Related U.S. Application Data

(60) Provisional application No. 62/660,275, filed on Apr. 20, 2018, provisional application No. 62/512,752, filed on May 31, 2017.

(51) Int. Cl.
*A61M 15/00* (2006.01)
(52) U.S. Cl.
CPC .... *A61M 15/0028* (2013.01); *A61M 15/0008* (2014.02); *A61M 15/0021* (2014.02);
(Continued)
(58) Field of Classification Search
CPC .......... A61M 15/0028–0041; A61M 15/0008; A61M 15/0021; A61M 15/0086;
(Continued)

(56) References Cited

U.S. PATENT DOCUMENTS 3,856,185 A 12/1974 Riccio
5,673,686 A 10/1997 Villax et al.
(Continued)

FOREIGN PATENT DOCUMENTS

DE 102014017409 A1 6/2016
RU 2610779 C1 2/2017
(Continued)

*Primary Examiner* — Elliot S Ruddie
(74) *Attorney, Agent, or Firm* — WC&F IP

(57) ABSTRACT

Containment units, dry powder inhalers, delivery systems, and methods for the same are disclosed. Exemplary devices are configured to have inlets and outlets which are formed with the containment walls of a containment unit. Air jets formed by the configuration of inlet(s) and outlet(s) inside the containment unit create significant turbulence and deaggregate the powder. Delivery system components downstream of the containment unit may integrate the exiting aerosol plume with a low flow nasal cannula air stream for delivery to a subject.

34 Claims, 9 Drawing Sheets

(52) U.S. Cl.
CPC .... *A61M 15/0086* (2013.01); *A61M 15/0091* (2013.01); *A61M 2202/064* (2013.01); *A61M 2206/16* (2013.01)

(58) Field of Classification Search
CPC ........ A61M 15/0091; A61M 2202/064; A61M 2206/16; A61M 11/02; A61M 15/0061; A61M 16/0672; A61M 2016/0021; A61M 2016/0027; A61M 2205/3334; A61M 2206/11; A61M 2206/18; A61M 16/14; A61M 15/003
USPC .................................................. 128/203.15
See application file for complete search history.

(56) References Cited

U.S. PATENT DOCUMENTS

| | | | |
|---|---|---|---|
| 5,845,776 | A | 12/1998 | Galbierz et al. |
| 6,341,605 | B1 | 1/2002 | Ohki et al. |
| 6,543,448 | B1 | 4/2003 | Smith et al. |
| 6,880,555 | B1 | 4/2005 | Brunnberg et al. |
| 7,461,649 | B2 | 12/2008 | Gamard et al. |
| 7,722,566 | B2 | 5/2010 | Tsutsui |
| 7,832,399 | B2 | 11/2010 | Ganem et al. |
| 8,522,775 | B2 | 9/2013 | Malhotra et al. |
| 8,677,992 | B2 | 3/2014 | Villax et al. |
| 2002/0144680 | A1* | 10/2002 | Nilsson ............... A61M 15/005 128/203.15 |
| 2006/0147389 | A1 | 7/2006 | Staniforth et al. |
| 2006/0254583 | A1 | 11/2006 | Deboeck et al. |
| 2007/0151562 | A1 | 7/2007 | Jones et al. |
| 2009/0084379 | A1 | 4/2009 | Goeckner et al. |
| 2010/0108062 | A1 | 5/2010 | Ganem et al. |
| 2012/0145150 | A1 | 6/2012 | Donovan et al. |
| 2012/0298106 | A1* | 11/2012 | Kjellgren .......... A61M 15/0043 128/203.15 |
| 2014/0053831 | A1* | 2/2014 | Leamon ............ A61M 16/0833 128/200.14 |
| 2014/0290654 | A1* | 10/2014 | Poole ...................... A61K 9/14 128/203.23 |
| 2017/0165439 | A1 | 6/2017 | Kaufmann |

FOREIGN PATENT DOCUMENTS

| | | |
|---|---|---|
| WO | 2005065756 A2 | 7/2005 |
| WO | 2007018568 A1 | 2/2007 |
| WO | 2009009013 A2 | 1/2009 |

* cited by examiner

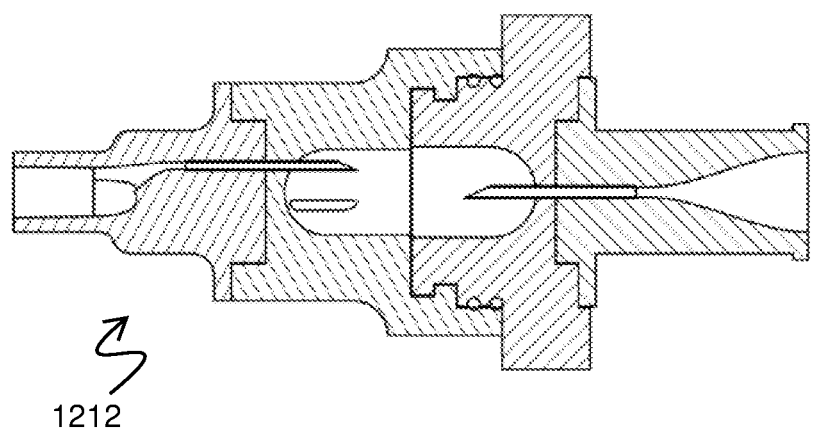
1212
Figure 12
Figure 13

DEVICES, SYSTEMS, AND METHODS FOR DRY POWDER THERAPIES

CROSS-REFERENCE TO RELATED APPLICATIONS

This application claims the benefit of U.S. Provisional Patent Application Nos. 62/512,752, filed May 31, 2017, and 62/660,275, filed Apr. 20, 2018. The complete contents of both provisional applications are herein incorporated by reference.

STATEMENT REGARDING FEDERALLY SPONSORED RESEARCH OR DEVELOPMENT

This invention was made with government support under Grant Nos. 2R01HL107333-05A1, R01HD087339, and R01HL139673 awarded by the National Institutes of Health. The government has certain rights in the invention.

FIELD OF THE INVENTION

The invention generally relates to dry powder devices, in particular, devices, systems, and methods with exemplary deaggregation and anti-device depositional properties.

BACKGROUND

Dry powder inhalers, which are used for generating and delivering pharmaceutical aerosols from powders, frequently use capsules or blisters. Advantages of capsules or blisters include a method to protect each dose from the environment, low cost, and operation in different DPI devices. Capsules are well-developed, come in multiple materials and sizes, are easy to fill, and work with standard pharmaceutical industry processing (e.g., filling) equipment.

With known capsule or blister DPIs, the capsule or blister may be pierced with needles (sharpened solid rods) that extend into the capsule or blister and then retract when the user pushes a button on the device. Alternatively, the capsule or blister may be torn open by the DPI or cut. In most devices, piercing or opening the capsule or blister requires an additional step beyond loading into the device and prior to inhalation. In devices which use a piercing element that is retracted prior to emptying the powder, one or more flaps of material from the punctured barrier may partially or wholly cover the openings made by the piercing element after the piercing element is retracted. In some prior devices, the piercing needle is hollow and may remain in a capsule to serve as a conduit. In such cases, the piercing action can result in a capsule flap which may still interfere with flow at the needle's opening. Furthermore, in some cases the piercing element is undesirably introduced to the interior of the capsule at the same location as a powder bed.

The PennCentury Insufflator is used for laboratory animal testing. Disadvantages of the Insufflator include non-acceptance of preloaded capsules and less than exemplary powder dispersion.

Researchers and companies performing inhalation toxicology testing with in vitro cell cultures need an effective way to produce a powder aerosol for cell exposure. There is also an immediate need in the area of animal safety and efficacy testing of inhalation products.

To operate DPIs with positive pressure, complete commercial DPI's have been placed in positive pressure enclosures. Some previously disclosed inline (active) DPIs work with large air volumes (e.g., 1 L) supplied by a ventilation bag.

A variety of problems are known for existing DPI devices. As one problem, if all air passes directly through the powder bed, the powder will be aerosolized too quickly leading to poor deaggregation performance. There are other shortcomings of aerosolizing the powder too quickly including high mouth-throat deposition. This problem is either ignored by existing devices (with the result that all airflow passes directly through the powder bed) or else addressed using bypass (side) airflow channels. The latter solution can sometimes alleviate the problem but fail to resolve it and add undesirable complexity.

Capsules have for decades been a standard means of encapsulating certain medicines administered orally and absorbed via the digestive tract. Their prevalence and well-established manufacturing processes made them an easy but less than optimal choice for dry powder medicaments which are administered via the respiratory tract.

Simultaneous administration of a pharmaceutical aerosol through noninvasive ventilation systems and into the lungs (nose-to-lung or N2L delivery) is viewed as convenient and prevents the removal of ventilator support during aerosol delivery. However, aerosol delivery efficiency through small diameter tubing and cannula systems is known to be very low, with typical values in the range of 0.6-2.5% of the loaded dose even at flow rates of 2-5 L/min (LPM).

SUMMARY

Exemplary embodiments comprise containment units for dry powders, dry powder inhalers (DPIs), and delivery systems for delivering dry powders to subjects.

According to an aspect of some exemplary embodiments, a containment unit (CU) is configured to maximize deaggregation of dry powder and entrainment thereof in the air flow leaving the containing unit. In some embodiments, the inlet and outlet apertures of the CU are positioned, sized, and arranged relative to one another to provide a direct airflow path which does not directly pass through a dry powder bed.

According to an aspect of some exemplary embodiments, direct air flow path is defined according to inlet jet momentum. A predefined threshold of momentum may be defined to differentiate the presence or absence of an inlet jet at a particular location in space. The predefined threshold may be characterized quantitatively using a Reynold's number.

According to an aspect of some exemplary embodiments, the dry powder contained within a CU is formulated to move freely under the effects of gravity and absent substantial air flows. The interior space of an exemplary CU, as defined by one or more containing walls, permits the dry powder to form a powder bed that is outside a direct air flow path when the CU is in an orientation of use. An orientation of use may be, for example, vertical or horizontal (relative to the gravitational vector or relative to ground) or some other predefined angle.

According to an aspect of some exemplary embodiments, the inlet and outlet apertures of a CU are sized to produced secondary airflows within the CU. Secondary airflow(s) may be established strictly by a mismatch of inlet and outlet diameters. The inlet aperture may be smaller than outlet aperture. The inlet aperture may have a smaller diameter than the outlet aperture. The cross sectional area of all inlet apertures may be smaller than the cross-sectional area of all outlet apertures.

The overall shape of a CU is particularly suited for maximizing powder deaggregation. In this respect a CU may differ substantially from DPI capsules known in the art. Some CUs according to the invention are not physically damaged by piercing, crushing, puncturing, crushing, rupturing, or cutting as are known dry powder capsules and blisters. Thus while exemplary CUs may be disposable (e.g., after single use), they may also in some cases be reused or conveniently recycled.

According to an aspect of some exemplary embodiments, a CU is configured as a standalone vessel for containing and protecting a dry powder until such time it is administered to a user (e.g., a patient). A multiuse inhaler may be configured to receive multiple CUs (consecutively or concurrently). In other exemplary embodiments, a CU and inhaler may be integral and disposed of together. A disposable inhaler may be single-use or multi-use depending on the number CUs it contains (e.g., one or more than one).

According to an aspect of some exemplary embodiments, a DPI is configured to operate with relatively low volume (LV). The airflow volume through all inlet apertures is typically low compared with an inhaled breath, e.g., on the order of 1-200 ml, with typical airflow volumes on the order of 3-50 ml. Low air volumes are needed when delivering aerosols to infants and children (10-50 ml). Low air volumes are needed when delivering aerosols to test animals (5 ml and below). In some embodiments, all actuation airflow passes through the inlet(s) and containment unit. One benefit of this configuration is that the device is actuatable with small air volumes.

Embodiments of the invention may comprise active DPIs, passive DPIs, and inline DPIs for adults. Embodiments of the invention may comprise delivery of dry powder aerosols during mechanical ventilation, delivery of dry powder aerosols to infants and children, and delivery of dry powder aerosols to laboratory test animals for drug safety and efficacy testing.

Some embodiments exhibit the advantage of reducing the powder delivery rate which leads to improved deaggregation (smaller outlet particle size). Additional advantages of reduced delivery rate in some exemplary embodiments include (a) reduced potential for the momentum cloud effect leading to unwanted deposition, (b) reduced potential for electrostatic cloud effects leading to unwanted deposition, and (c) improved hygroscopic growth of excipient enhanced growth (EEG) formulations.

A delivery system may comprise conduits and ports which facilitate movement of the dry powder from an opened CU to a subject's respiratory system.

A spacer may be provided in a delivery system for controlling the aerosol plume exiting the DPI device and transporting the powder downstream of the DPI through the delivery system. The spacer may be configured to integrate an aerosol plume from a DPI into the low velocity gas stream of a low flow nasal cannula (LFNC) or high flow nasal cannula (HFNC) system. The ventilation gas of the LFNC stream may be operated continuously without interruption from the temporary administration of an aerosol from the inhaler.

BRIEF DESCRIPTION OF THE DRAWINGS

FIG. 10. Straight-through (ST) containment unit illustrating the powder bed (in an orientation of use) not in the pathway of the direct inlet airflow.

FIG. 11. Single-sided (SS) containment unit illustrating the powder bed (in an orientation of use) in the pathway of the direct inlet airflow.

FIG. 12. DPI with CU having three inlet orifices and one outlet orifice.

FIG. 13. Cross-section of three inlet orifices from DPI/CU of FIG. 12.

FIG. 14. Delivery system for aerosol delivery during low flow nasal cannula (LFNC) therapy.

FIG. 15. Spacer used to integrate the aerosol plume from the containment unit DPI with ventilation gas delivered to a patient. The containment unit DPI emits aerosol that enters at the device inlet. The ventilation gas enters at the air inlet.

DETAILED DESCRIPTION

Figure 1:
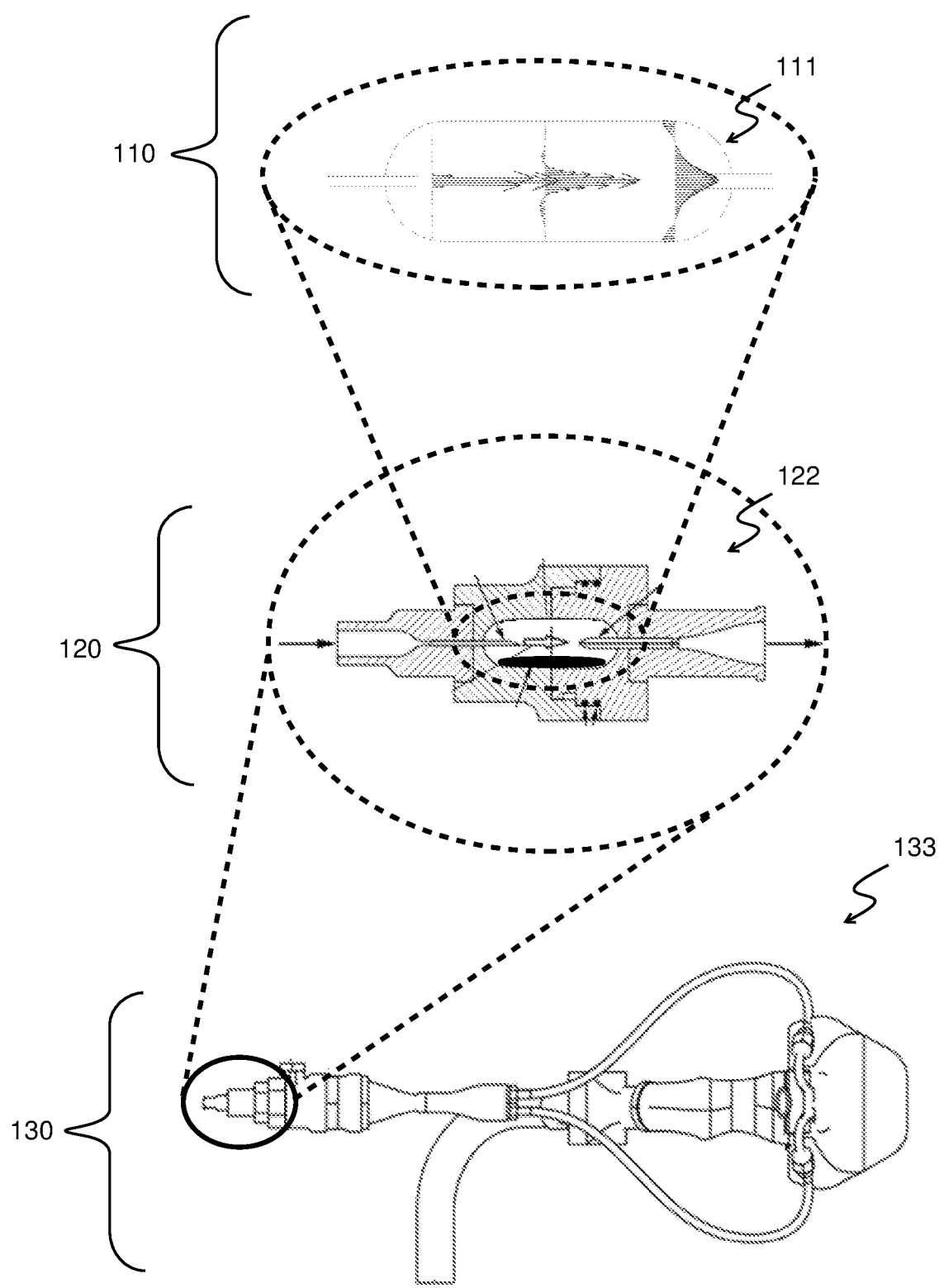
FIG. 1. Device and system levels which embody some exemplary embodiments.

FIG. 1 depicts three levels from which exemplary embodiments will be described below. The first level 110 is a containment unit (CU) 111. The second level 120 is a dry powder inhaler (DPI) 122. The DPI 122 is configured to accommodate a CU 111. The third level 130 is a delivery system 133. The delivery system 133 may comprise the DPI 122. For at least low volume (LV) respiratory therapies, a delivery system 133 may include most if not all of the hardware components which contribute to the flow pathways from their initiation to the point of administration to the subject.

FIGS. 2-9 provide details at the first level 110 of FIG. 1. The figures discuss aspects of exemplary containment units (CUs).

Containment units may be configured according to a number of inlet orifices (e.g., one, two, three, or some other number), a number of outlet orifices (e.g., one, two, three, or some other number), dispersion air flow path (e.g., same-side (SS) and straight-through (ST)), volume, inlet and outlet internal diameters, inlet and outlet protrusion length, protrusion direction, fill mass, shape, and other aspects.

FIGS. 2 to 6 show alternative exemplary CUs. CUs 200, 300, 400, 500, and 600 each comprise one or more containing walls 210, 310, 410, 510, and 610. The containing walls enclose and protect a dry powder 220, 320, 420, 520, or 620 from external conditions (e.g., moisture, humidity, airborne contaminants). The containing walls may also be responsible for defining the overall shape and body of the CU and most or all of the boundaries which define the interior space and total (internal) volume of a CU. The containing walls may hermetically seal the contents of the CUs. The dry powder is or contains a medicament for oral inhalation or nasal administration to a subject.

CUs 200, 300, 400, 500, and 600 further comprise inlets and outlets. In particular, each CU comprises one or more inlets and one or more outlets. The combination of at least one inlet and at least one outlet may provide a continuous flow passage through the containment unit. In some embodiments a containment unit may have a plurality of inlets and/or a plurality of outlets.

An "inlet" is one or more structural elements which, at a minimum, define an orifice through which matter (e.g., a gas) may flow. Similarly, an "outlet" is one or more structural elements which, at a minimum, define an orifice through which matter (e.g., gas and entrained powder particles) may flow. An inlet may further comprise a protrusion that extends inwardly or outwardly. For an inlet, an inward protrusion allows for moving a powder bed out of direction airflow pathway when the use orientation is vertical. An outward protrusion may improve emptying of the CU (e.g., as measured as percentage of powder removed on a single actuation). An outlet may further comprise a protrusion that extends inwardly or outwardly. For an outlet, an inward protrusion advantageously reduces size, whereas an outward protrusion may improve emptying of the CU.

Whether in regard to an inlet or an outlet, an inward protrusion extends from a surface (e.g., of a containing wall) toward or partially toward the CU's center. An outward protrusion extends from a surface (e.g., of a containing wall) away or partially away from the CU's center. Illustrated embodiments herein mainly disclose protrusions of circular cross-section, and some protrusions may be referred to as capillaries. Protrusions may have cross-sectional shapes other than circular, e.g., oval, oblong, square, rectangular, polygonal, or some other shape. Protruding inlets and outlets may be used to ensure that the powder remains in the containment unit until actuation occurs, may help ensure that no part of the powder bed is in the path of the direct inlet airflow, and/or may improve aerosolization behavior.

Inlet or outlet protrusion length may vary, e.g., between 0 mm and 90 mm, or 40-90 mm, or 45-90 mm, for example. The exact length may vary depending on the internal volume of the containment unit, which in turn may depend on the dry powder mass required to be delivered. In general, outlet protrusion length may present a tradeoff between deaggregation effects and emitted dose (ED). Longer protrusion lengths (e.g., 45 mm versus 90 mm) are better at deaggregating the spray dried powder but may result in lower emitted dose (ED).

CUs may be configured to have a particular orientation of use (i.e., use orientation). The orientation of use is a preferred or required orientation of the CU at the time its dry powder contents are evacuated. By contrast, when in a sealed storage state the orientation of the CU may be any orientation.

Figure 2:
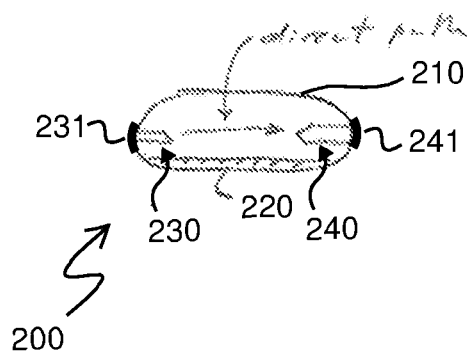
FIG. 2. An exemplary containment unit with inwardly protruding inlet and outlet with a horizontal use orientation.

FIG. 2 is an exemplary containment unit 200 shown in cross-section. The CU 200 comprises an inwardly protruding inlet 230, inwardly protruding outlet 240, and horizontal use orientation. The arrow shows a primary flow path and illustrated that a direct path exists between the inlet and outlet which does not pass through the powder bed 220. The arrangement of inlet and outlet at opposite ends, especially opposite longitudinal ends, of the body of the CU may be referred to as a straight-through (ST) configuration.

During storage or prior to administration, an exemplary CU may be sealed (e.g., hermetically sealed), thereby ensuring the dry powder is not exposed to environmental parameters like high humidity. One or more removable seals may be provided. In the case of CU 200 of FIG. 2, seals 231 and 241 are configured to seal the inlet 230 and outlet 240, respectively, when the CU 200 is storing the dry powder 220 (between the time of manufacture and the time of administration to a subject).

Exemplary seals are foil covers or screw caps. For a straight-through (ST) device a seal such as a screw cap may be arranged at each distal end of a CU. For a same-side (SS) device a pair of seals or a single seal may be arranged to seal off communication to the external environment from both the inlet and outlet. To use a CU (that is, to administer the dry powder contained in the CU), the seal (e.g., foil or screw cap) may be removed by a user or by an inhaler into which the CU is loaded. Inhalers, in particular dry powder inhalers (DPIs), belong to the second level 120 (FIG. 1) and are discussed in greater detail below.

Figure 3:
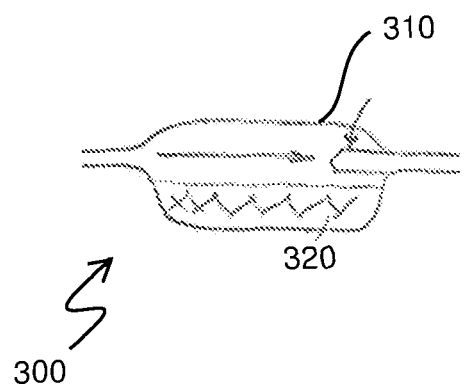
FIG. 3. An exemplary containment unit with an outwardly protruding inlet and inwardly protruding outlet with a horizontal use orientation.
Figure 4:
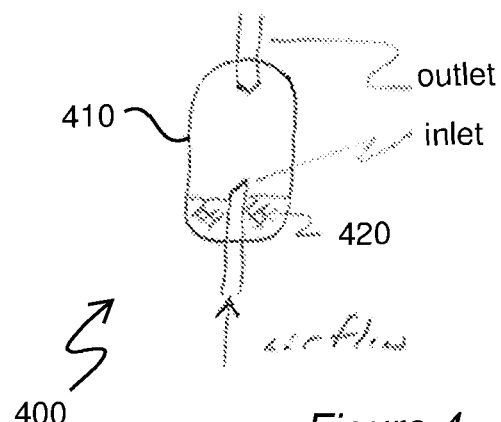
FIG. 4. An exemplary containment unit with inwardly protruding inlet and outlet with a vertical use orientation.
Figure 5:
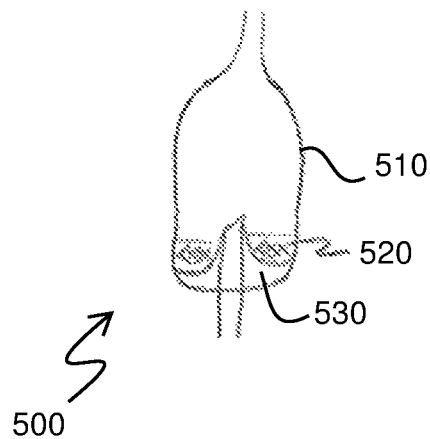
FIG. 5. An exemplary containment unit with an inwardly protruding inlet and an outwardly protruding outlet with a vertical use orientation. Smooth curves are used to connect the inwardly protruding inlet with the remaining CU walls.
Figure 6:
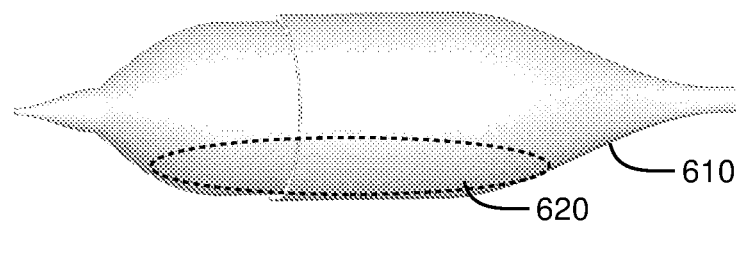
FIG. 6. An exemplary containment unit with outwardly protruding inlet and outlet with a horizontal use orientation.

FIGS. 3 to 6 illustrate CUs with alternative configurations from CU 200 of FIG. 2. FIG. 3 is an exemplary containment unit 300 with an outwardly protruding inlet, inwardly protruding outlet, and horizontal use orientation. As compared to CU 200, CU 300 also has an expanded capacity (e.g., for 100 mg dry powder as opposed to 10 mg dry powder) within the CU while keeping the primary airflow path (indicated by the arrow) apart from the powder bed 320. FIG. 4 is an exemplary containment unit 400 with inwardly protruding inlet, inwardly protruding outlet, and a vertical use orientation. Experimental evidence shows comparable performance between CUs 200 and 400 when they are similarly configured except for their orientation of use. FIG. 5 is an exemplary containment unit 500 with an inwardly protruding inlet, an outwardly protruding outlet, and a vertical use orientation. FIG. 5 also comprises a streamlined recessed region 530 which facilitates maximizing the emitted dose. FIG. 6 is an exemplary containment unit 600 with outwardly protruding inlet, outwardly protruding outlet, and a horizontal use orientation.

In some exemplary embodiments, the containment unit is fabricated as one piece of unitary construction, including the defined inlet(s) and outlet(s). A CU may be produced by, for example, 3D printing or injection molding. Inlets and outlets may be provided as integral parts of the CU. As a result, the inlets and outlets exist prior to opening the CU. This contrasts sharply with conventional capsules which have no identifiable inlet or outlet until after their walls are breached by a piercing or cutting element. In some embodiments, the inlets and outlets may be a different material than the containment walls but fixedly or permanently embedded in or with the containment walls.

Providing the inlets and outlets as integral parts of the CU, even before the CU has been opened, yields a number of significant benefits. For one, the configuration permits exclusion of any moving needles which are often necessary for piercing conventional capsule or blisters. Thus not only does an exemplary CU not have any external or exposed needles, it may have no needles whatsoever. Additionally, the inlets and outlets may have precisely controlled geometries which are not determined by any inhaler into which the CU is installed but rather by the CU itself. This constitutes a shift from conventional practice over which structural element of a delivery system is responsible for defining the orifices through which gases enter and exit a CU. The geometries and positions of the inlet and outlet orifices may be defined at the time of manufacture of the CU because they are built in to the geometry of the CU.

Sizes of inlets and outlets (e.g., the internal diameter of an inlet or outlet with a circular cross section) may be in the range of 0.4 to 2.4 or 3 mm. A size of 3 mm or greater may be needed in certain low pressure oral devices. This size may be measured at the orifice. The diameters may be configured to provide a controlled high speed micro jet (which may simply be referred to as a "jet" in this disclosure) at the inlet and filter large particles from exiting the outlet. These qualities help ensure production of a fine deagglomerated aerosol when the CU is evacuated. In some exemplary embodiments, the sizes of inlets and outlets, in particular their respective orifices, are different. An inlet orifice may be smaller than an outlet orifice, or an outlet orifice may be smaller than an inlet orifice. A larger outlet (e.g., measured by orifice diameter) relative to the inlet is advantageous in many embodiments in order to decelerate the inlet airflow and induce secondary velocities/flow in the containment unit. The secondary flows may improve dispersion and/or deaggregation of the powder bed.

The inlets and outlets provide a continuous flow pathway and means for the powder to exit the interior space of a containment unit without physically piercing, crushing, puncturing, crushing, rupturing, or cutting a containing wall. In addition, the configuration (e.g., size, shape, arrangement with respect to the interior space(s) of the containment unit, and arrangement with respect to other parts of the containment unit) of the inlets and outlets provide the hydrodynamic force needed to deaggregate powder. The hydrodynamic force takes the form of an inlet jet and secondary airflows.

The distance with which an inlet or outlet protrusion extends from a containment wall may be configured to maximize flow velocities near inlet walls and minimize powder deposition near the inlet or outlet base (e.g., where the protrusion and containment wall meet). In some embodiments an exemplary inward protrusion distance is 2 to 10 mm, or in some cases 3 to 5 mm, e.g., 4 mm. As between two protrusion lengths, one longer and one shorter, the shorter protrusion may reduce shear forces associated with the outlet orifice due to the orifice's closer position to the containment wall.

Figure 7:
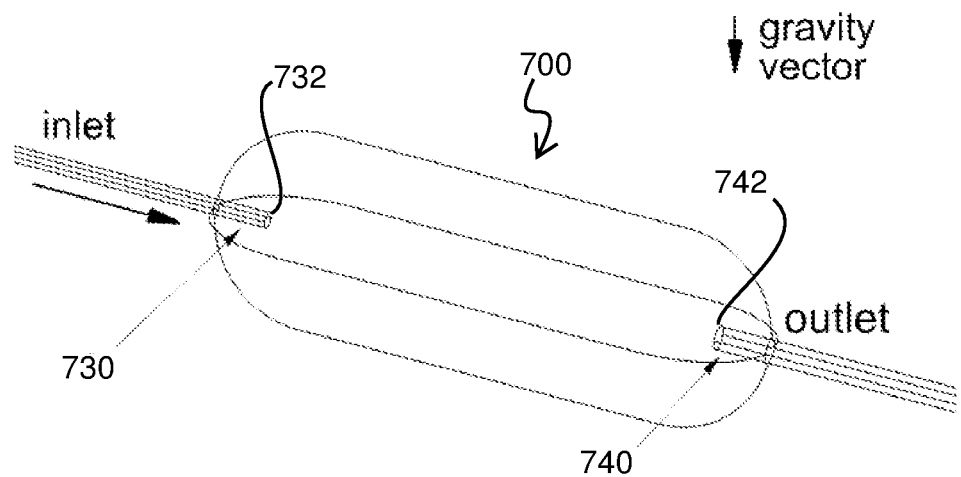
FIGS. 7-9. Computation fluid dynamic (CFD) modeling of an exemplary containment unit. The direct airflow pathway is illustrated as well as secondary (or indirect) flows that are used to initially aerosol the powder from the powder bed.
Figure 8:
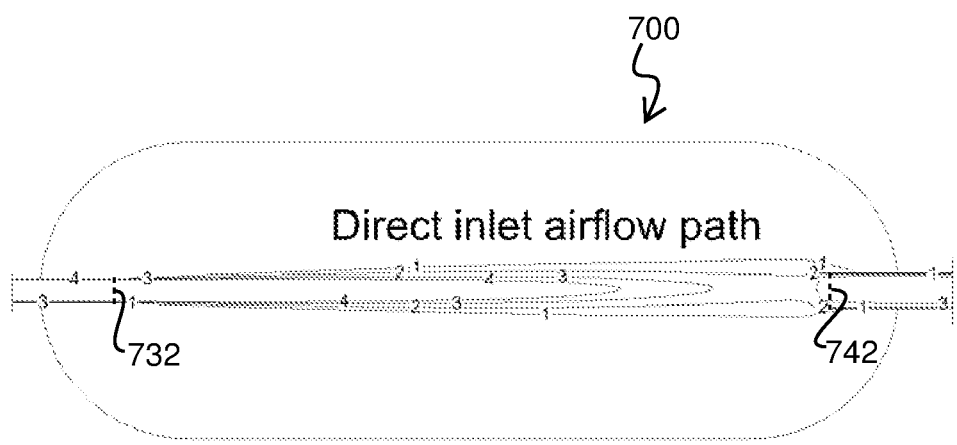
Figure 9:
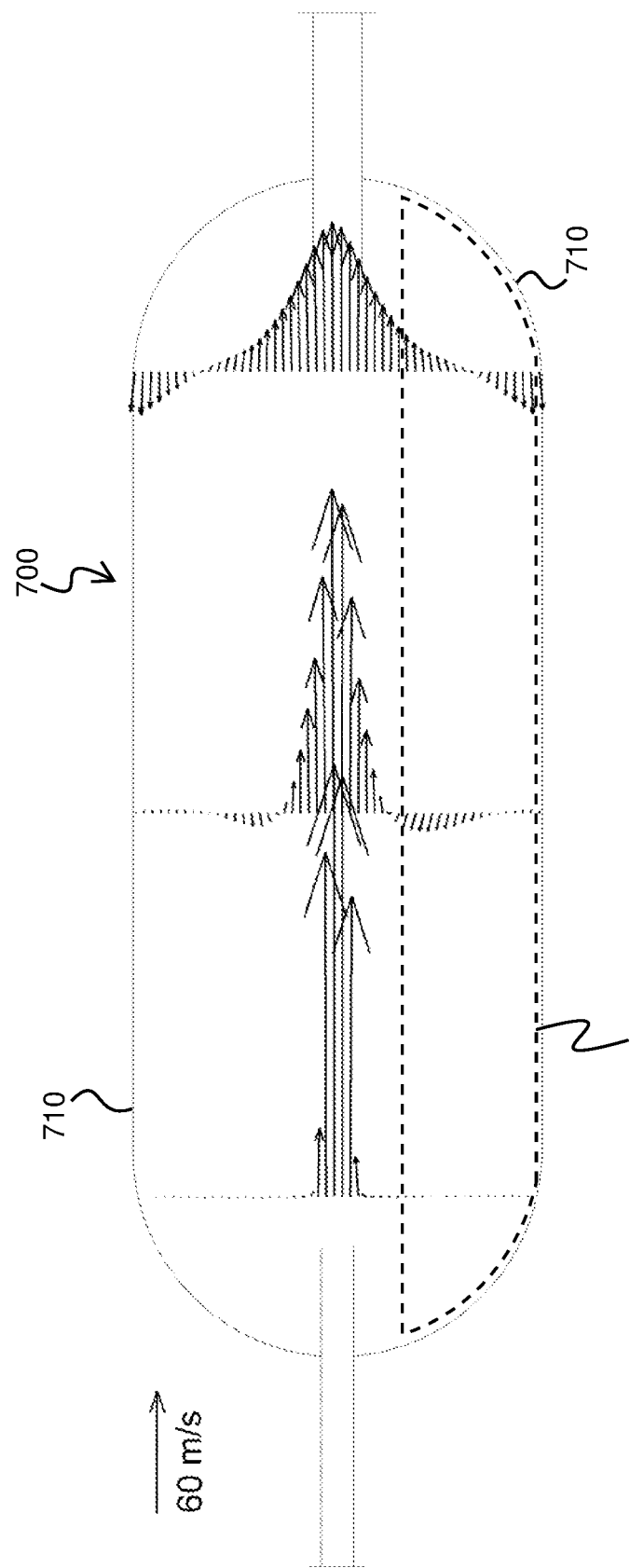

FIGS. 7-9 are illustrations from a computation fluid dynamic (CFD) model of an exemplary containment unit. The direct airflow pathway is illustrated as well as secondary (or indirect) flows that are used to initially aerosolize the powder from the powder bed.

FIG. 7 illustrates a direct inlet airflow path within a containment unit 700. The airflow path is a geometric path from the embedded inlet 730 (in particular the inlet orifice 732) to the embedded outlet 740 (in particular the outlet orifice 742). The direct inlet airflow path within the containment unit may be defined as a path of airflow aligned with the inlet which, due to momentum, continues on a straight line until it reaches a boundary or outlet. At least a portion of the direct inlet airflow path may be characterized as an "inlet jet". Any remaining portion of the path is not an inlet jet. A Reynolds number (Re) threshold may be used to define a boundary in space up to which an inlet jet exists and beyond which the inlet jet no longer exists. For a jet to occur and move through a majority of space of a CU, the Re may preferably be 100 or greater. For Re<100, the jet will only move through a portion of the CU. The inlet jet can be assumed to end at a location in which the secondary velocities (reverse flow) on a plane normal to the inlet jet are greater than the velocity of the inlet jet. Reynolds number may be determined according to the following equations:

$$Re \equiv \frac{\text{inertial forces}}{\text{viscous forces}}$$

$$Re = \frac{\rho V_{jet} D_{jet}}{\mu}$$

where
$\rho$=air density≈1.17 kg/m³,
$V_{jet}$=inlet jet velocity,
$D_{jet}$=inlet orifice diameter,
$\mu$=dynamic viscosity of air=183.7×10⁻⁷ (N·s/m²).

Note that Re is a non-dimensional parameter. Table 1 contains sample Reynold numbers for various prototypes.

TABLE 1

| Q(L/min) | $D_{jet}$ (mm) | A (mm²) | $V_{jet}$ (m/s) | Re |
|---|---|---|---|---|
| 3 | 0.4 | 0.126 | 399 | 10,137 |
| 3 | 0.6 | 0.283 | 177 | 6,758 |
| 3 | 1.0 | 0.785 | 63.7 | 4,055 |
| 15 | 1.0 | 0.785 | 318.3 | 20,274 |
| 15 | 2.0 | 3.14 | 79.6 | 10,137 |
| 15 | 3.0 | 7.07 | 35.4 | 6,758 |

Some CUs may be configured such that inlet flow forms an air jet aligned with the inlet orifice. For instance, the inlet jet's center axis may be coaxial with an inlet's center axis. An inlet jet may traverse a majority of the containment unit (e.g., travel at least 50% of the distance between an inlet orifice and an outlet orifice or containment unit wall directly opposite the inlet orifice). An inlet jet may traverse at least 50%, at least 60%, at least 70%, at least 80%, at least 90%, or 100% of the distance between an inlet orifice and an outlet orifice or containment unit wall directly opposite in the inlet orifice. An inlet jet may traverse no more than 60%, no more than 70%, no more than 80%, no more than 90%, or no more than 99% of the distance between the inlet orifice and an outlet orifice or containment unit wall directly opposite the inlet orifice. The exact configuration desired for a particular CU depends on various aspects such as the relative positions of inlet/outlet orifices and the location of the powder bed. Regardless of the configuration of the inlet jet, in many embodiments it is desired that the inlet jet at no point make contact with the powder bed. More generally, in some embodiments it may be preferable that the powder is not in the direct path of the inlet air jet (e.g., a linear path corresponding with the flow path of inlet jet but which may extend past the end of the inlet jet).

FIG. 8 illustrates contours of velocity magnitude at four different levels, taken along a midplane splice of a CU for purposes of yielding a two-dimensional image at an inlet Reynolds number of 6,758. As illustrated in the figure, a central core of high velocity flow arises due to momentum that continues in a straight line from the inlet. This core of high velocity holds together tightly through the containment unit. Some deceleration of flow is observed as the flow approaches a larger diameter outlet which must have a lower velocity in order to satisfy conservation of mass. The momentum of the air jet and decelerating flow create secondary (or indirect) velocity motion surrounding the central jet core of direct airflow.

FIG. 9 further illustrates a direct inlet airflow pathway and secondary flows for CU 700 with an inlet Reynolds number of 6,758. FIG. 9 illustrates velocity vectors at three slices within the containment unit 700. First, it is observed that the direct inlet airflow pathway continues from the inlet to the outlet, as does the inlet jet in this case. Second, this direct airflow path generates secondary flows through a remainder of the containment unit, which move in the direction opposite of the direct inlet airflow pathway. The interior space 912 within the containing walls 710 permit the dry powder to form a powder bed that is outside the direct airflow path(way) when the containment unit is in an orientation of use (horizontal in FIG. 9). By removing the powder bed from the direct airflow pathway, secondary flows are used to initially deaggregate the powder slowing the rate of aerosol production and improving aerosol deaggregation. As illustrated in FIG. 9, a larger outlet diameter relative to the inlet diameter decelerates the inlet airflow and increases secondary velocities in the containment unit. These secondary velocities are used to aerosolize the powder bed. Some secondary velocity is desirable; however, too much (e.g., secondary velocities of too great a magnitude) may aerosolize the powder too quickly and start to increase particle size. It is this same reason that many CUs are preferably configured so that the primary inlet jet (which is generally the largest magnitude flow in the CU) does not pass through the powder bed in an orientation of use. Control of other device parameters discussed herein, such as the specific sizes of the inlet and outlet orifices or the fill mass, may be consequential to the performance of some embodiments so that the flows (inlet jet and secondary flows) and their magnitudes are precisely defined and controlled.

Following are exemplary parameters usable in a computation fluid dynamics (CFD) simulation for producing FIGS. 7-9. The model may use a 3 L/min airflow through a containment unit with a 0.6 mm orifice diameter inlet and a 0.89 orifice diameter outlet. The containment unit has an elliptical shape with a volume of approximately 0.68 ml. A fixed or embedded air inlet has an orifice diameter of 0.6 mm and protrudes into the containment unit approximately 2 mm. The embedded outlet has a diameter of 0.89 mm and protrudes into the containment unit approximately 2 mm. A fixed inlet flow rate of 3 L/min was implemented, which is consistent with the actuation of a 10 ml syringe filled with air over approximately 0.2 s. The simulations accounted for turbulent, compressible, and time varying airflow features. A hexahedral grid was employed that was tested to ensure grid convergent results.

In some instances a CU may be referred to as a "dose containment unit" (DCU) which implies the CU contains a predetermined dose of medicament. The dry powder within a CU may be any of a variety of formulations and medicaments. A dry powder of an embodiment may contain, for example, one or more of surfactants, antibiotics, osmotic agents, mucolytics, and anti-inflammatories. A standard formulation useful for testing purposes is a spray dried albuterol sulfate (AS) excipient enhanced growth (EEG) formulation containing drug (AS), mannitol, L-leucine, and poloxamer 188 in a ratio of 30:48:20:2% w/w spray dried using a Büchi Nano spray dryer B-90 (Büchi Laboratory-Techniques, Flawil, Switzerland). Some exemplary CUs and delivery systems are configured to accommodate and administer powder masses in the range of 1-50 mg, or 2-10 mg. Higher (e.g., up to 100, up to 200, up to 400 mg) and lower (e.g., down to 0.5, down to 0.25 mg, etc.) fill masses are also possible. In some embodiments the fill mass is ≥10 mg of dry powder.

An exemplary containment unit has an elliptical shape, e.g., according to the exterior which is defined by one or containing walls. The volume of a CU is preferably small which helps minimize overall inhaler system volume. In some embodiments an exemplary internal volume of a CU is 0.2 to 2.0 ml, in some cases 0.5 to 1.0 ml, e.g., 0.68 ml. In some prototype embodiments a preferred internal volume was found to be smaller than 0.68 mL. Holding other parameters constant, in a single-side (SS) DPI setup reducing the powder chamber volume from 0.68 mL (the internal volume of a size 0 capsule) to 0.21 mL doubled the % emitted mass after one actuation (p=0.0048) with a mean (SD) Dv50 of 2.5 μm and a submicrometer particle fraction of 28.8%.

FIGS. 10 to 14 illustrate aspects of the second level 120 of FIG. 1. In particular, FIGS. 10 to 14 discuss aspects of exemplary inhaler systems, in particular dry powder inhaler (DPIs). Embodiments of the invention may comprise active DPIs, passive DPIs, and inline DPIs. An inline DPI may create a pharmaceutical aerosol using a gas stream supplied from a positive pressure source, such as an air-filled syringe or manual ventilation bag. An exemplary inline DPI device may be operated with an air syringe containing small volumes, e.g. 10 mL, of room condition air.

Figures 10, 11:
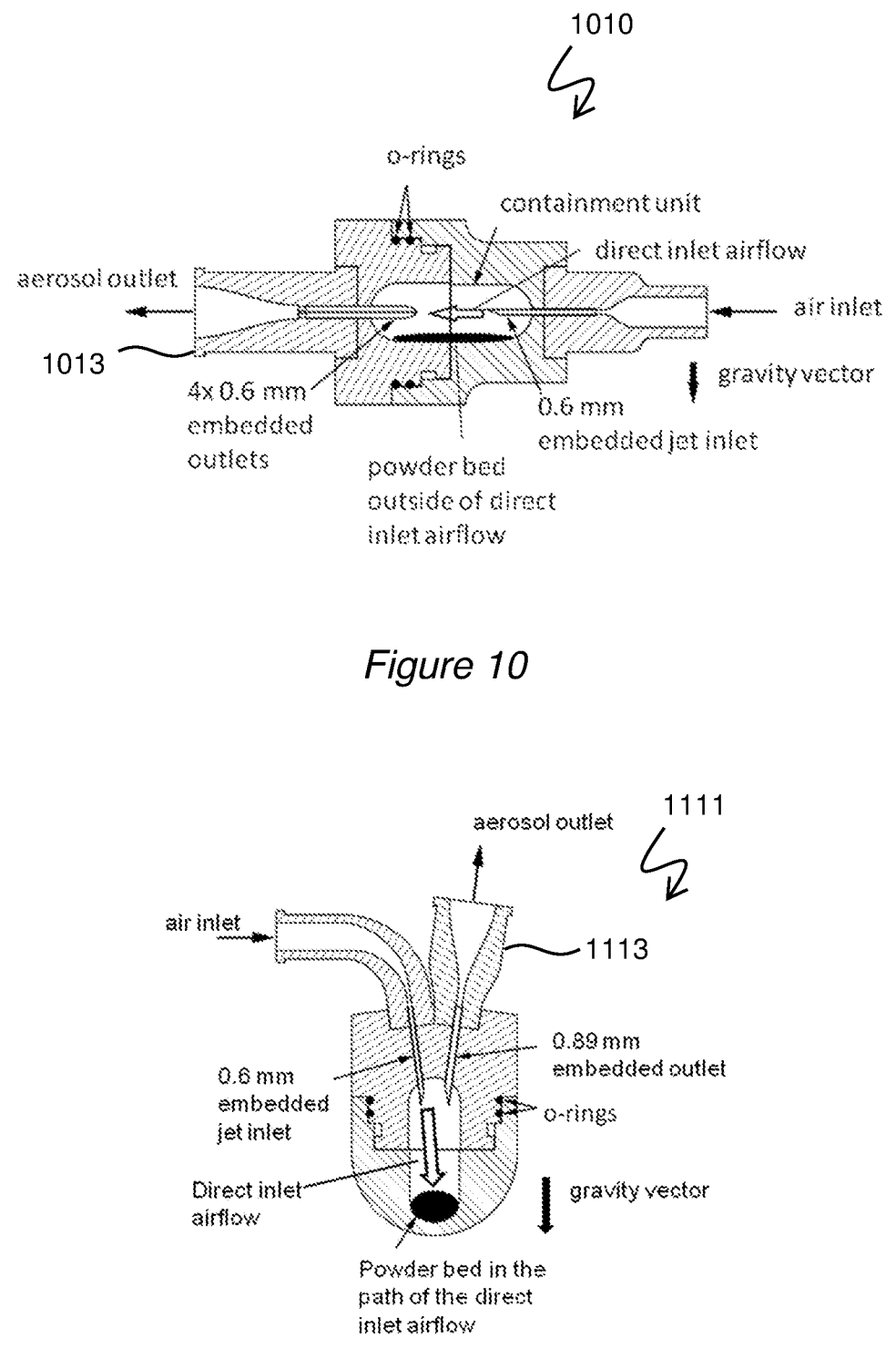

FIGS. 10 and 11 illustrate two prototypical containment unit DPIs 1010 and 1111. These prototype devices were manufactured in separate pieces, but commercial embodiments may be constructed as single units. FIG. 10 shows a DPI 1010 with straight-through (ST) dispersion airflow path. In this device the powder bed is not in the path of the inlet airflow. Inlet and outlet are opposite ends of the containment unit. An exemplary prototype device having features corresponding with DPI 1010 produced a DPI emitted dose of 57%, mass median aerodynamic diameter (MMAD) of 1.6 μm, and a fine particle fraction (FPF) less than 5 μm of 93.7%. This device was characterized by a 0.6 mm diameter inlet and a 1.17 mm diameter outlet, which both protruded inward by 6 mm. The inlet Reynolds number was 6,758.

FIG. 11 shows a DPI 1111 with a single-sided (SS) dispersion airflow path. In contrast to a ST configuration, with a single sided (SS) device, the inlet airflow may be aimed directly at the powder bed (e.g., as determined from the intersection of a center axis of the inlet orifice with the powder bed in an orientation of use and prior to its dispersal). However, structural and operation parameters may be controlled so that an inlet jet does not contact the powder bed during use (despite the flow pathway contacting the powder bed). A prototypical single-sided (SS) device developed to deliver powder aerosol with a low volume of dispersion air (10 mL per actuation) was observed to have a high emitted dose (87.9% of loaded dose) with a mass median aerodynamic diameter of 3.1 μm and a fine particle fraction less than 1 μm of the emitted dose ($FPF_{<5 \mu m/ED}$) of 61.6%.

DPI 1010 of FIG. 10 has a horizontal orientation of intended use (the center longitudinal axis of the cylindrical cavity is orthogonal to the gravity vector). DPI 1111 of FIG. 11 has a vertical orientation of intended use (the center longitudinal axis of the cylindrical cavity is parallel to the gravity vector).

To be loaded into an inhaler, the CU may be screwed or twist-locked in-line. For example, the inhaler body may separate in two with a twisting action, a CU containing the powder may be inserted, and the two parts of the inhaler body rejoined by a reverse twisting action.

The loading of the CU may automatically open the seals. For instance, the seals (e.g., seals 231 and 241 of CU 200 in FIG. 2) may be removed or broken when the delivery system is closed, thereby integrating the steps of closing the inhaler and opening the CU. This reduces the number of required steps for administration of the powder.

The inhaler into which the CU is loaded may comprise a streamlined exit configured to contain expansion of the aerosol plume and minimize depositional losses. DPI 1010 has a streamlined exit 1013, and DPI 1111 has a streamlined exit 1113.

DPI inhalers according to some exemplary embodiments are tailored for low dispersion air volume applications. Low dispersion air volume applications may be common among children (e.g., any young than approximately 5 or 6 years of age) and other subjects who lack the ability to properly use a conventional inhaler. Typically such subjects have low tidal volumes compared to healthy human adults.

FIG. 12 is a mid-plane cross-sectional view of a DPI device 1212 a CU for which has three inlets (left side) and one outlet (right side). FIG. 13 shows the pattern for the three inlets according to a transverse cross-sectional view. Inlet and outlet sizes may be determined based on the number of inlets and/or the number of outlets. For example, three inlets may each be 0.6 mm diameter and one outlet may be 0.89 mm in diameter. Depending on the application, net inlet flow may change with number of inlets. The largest secondary velocities will be formed if the total cross sectional outlet area is larger than the total cross sectional inlet area.

Figures 14, 15:
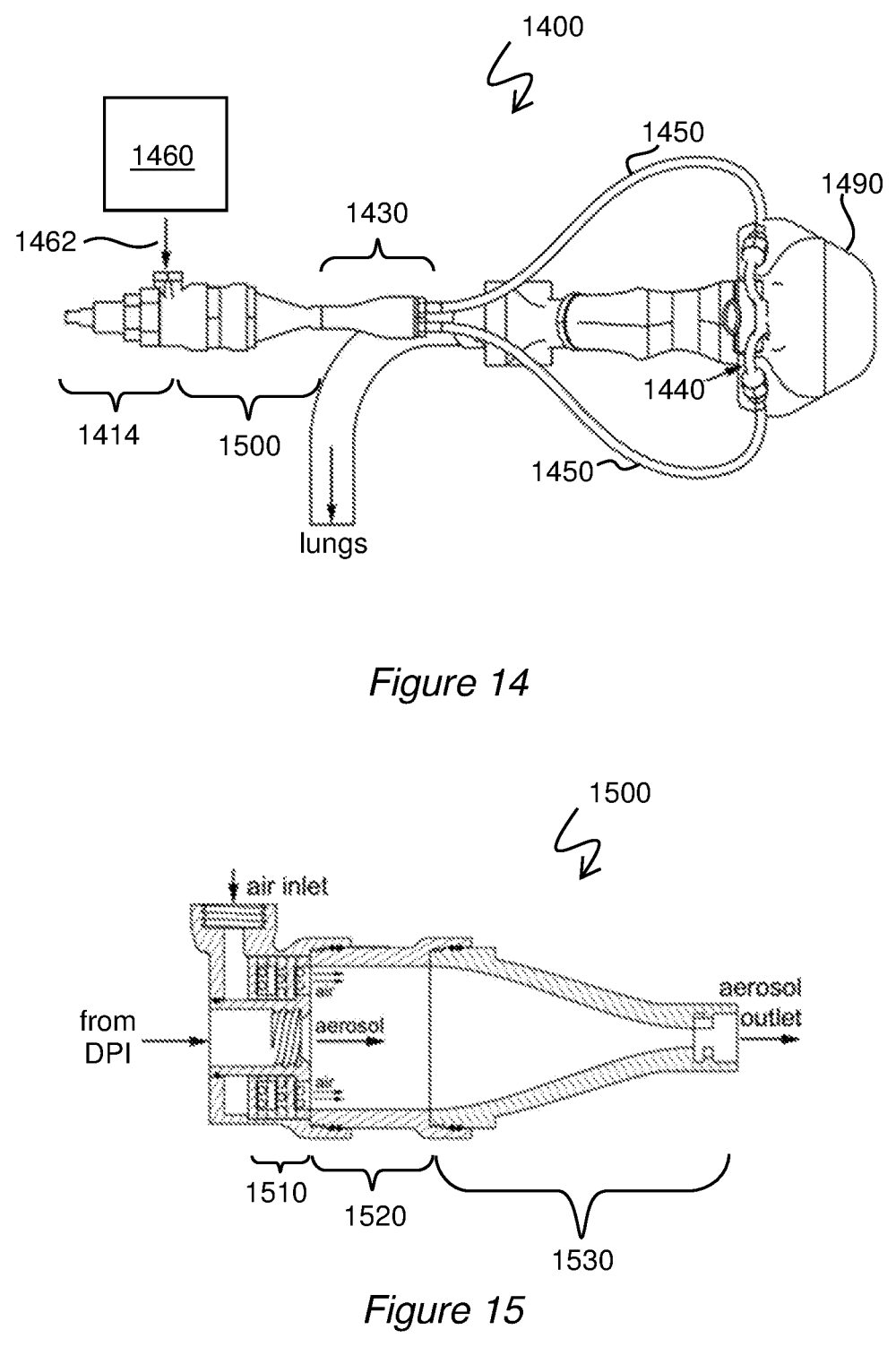

FIG. 14 illustrates details at the third level 130 of FIG. 1. In particular, FIG. 14 shows aspects of some exemplary delivery systems.

A low flow nasal cannula (LFNC) delivery system 1400 may comprise or consist of a containment unit (not visible in FIG. 14 from the system's exterior), a DPI 1414, a spacer 1500, a y-connector 1430 (preferably streamlined (SL)), and a cannula 1440 (preferably streamlined (SL)). The system 1400 may further include tubing 1450, a source 1460 of LFNC gas flow 1462. Each length of tubing 1450 connecting the Y-connector 1430 to the cannula 1440 may be approximately 60 cm long, a length sufficient to curve the tubing around a human subject's ears and allow the DPI and spacer to reside sufficiently far from the patient. The orifices of the cannula 1440 deliver the system's stream to the airways of a subject 1490. From there the aerosolized stream may continue to the lungs.

Important to total lung deposition is that the aerosol is delivered very rapidly. A primary advantage of using a dry powder device (DPI) in a delivery system like system 1400 over alternatives systems (e.g., those employing mesh nebulizers) is that a comparatively large medicament mass can be administered in a short amount of time. For example, an exemplary system may be configured to deliver a 10 mg powder mass in approximately 38 s (assuming a 7.5 s breathing cycle for deep inspiration) compared to a minimum 7 minute duration with a mesh nebulizer at a 0.5% drug concentration, not accounting for system losses.

For a prototype system corresponding with system 1400, the transit time (the time required for the aerosol to reach the cannula after syringe actuation) of the delivery system was similar for ventilation gas flows of 5 and 8 LPM and is approximately 0.2 s for both flow rates. However, delivery duration from the cannula (the duration of time that aerosol is exiting the cannula) was affected by the ventilation gas flow rate and at 5 and 8 LPM was approximately 0.75 and 0.5 s, respectively. This compact time window may enable actuation with the start of nasal inspiration. A delivery system 1400 may comprise a simple pressure monitor or flow direction element on the cannula to sense inspiratory or expiratory flow. Ideally, conscious subjects can be instructed to inhale deeply through the nose for a period up to 3 s, enabling all of the ex-cannula dose to enter the nose and be delivered to the lungs.

Some exemplary embodiments address shortcoming in the art to improve the performance (e.g., efficiency) of delivering dry powder formulations to a subject (e.g., a human, an animal, etc.). High efficiency performance for the delivery of EEG formulations may be defined by the production of an aerosol with the following characteristics: an MMAD of less than 1.5 µm, fine particle fraction (FPF) less than 5 µm as a percentage of ED ($FPF_{<5\ \mu m/ED}$) above 90%, $FPF_{<1\ \mu m/ED}$ above 30% and a device emitted dose (ED) greater than 75%.

Low dispersion air volume (e.g., ≤5 ml) actuation of some exemplary DPI devices may result in dense aerosol plumes exiting the DPI device. Depending on the subject (e.g., subjects with high tidal volumes versus low tidal volumes), direct administration of a dense aerosol plume to the subject's airways may lead to undesired impactions and depositional losses at incorrect locations of the respiratory system (e.g., losses in the trachea and bronchi instead of targeted alveoli). Accordingly, in some embodiments the combination of the DPI device with downstream components is advantageous. So-called spacers are one such component.

FIG. 15 shows an exemplary spacer 1500. Some embodiments may comprise a spacer configured to combine an aerosol stream with a low flow nasal cannula (LFNC) or high flow nasal cannula (HFNC) ventilation gas stream. The aerosol stream may be intermittent (e.g., supplied in one or more short bursts) and the ventilation gas stream may be continuous (e.g., supplied constantly and/or at a steady rate over a single time duration longer than a single burst of the aerosol stream or over a single time duration encompassing a plurality of bursts of the aerosol stream). Low flow oxygen nasal cannula therapy, or LFNC therapy, is a treatment that delivers oxygen to the nasal cavity at gas flow rates up to ~8 LPM in adults and ~1 LPM in children to treat hypoxemia. With LFNC therapy, the ventilation gas is typically not heated or humidified to maintain system simplicity and the flow rate remains low to avoid nasal discomfort associated with cold temperature and drying. For an inline DPI, it is generally preferred that a small amount of dispersion air volume be used to generate the aerosol as higher air flows will create impaction in small diameter tubing and potentially exceed the subject's inhalation flow rate.

The spacer 1500 may comprise an inlet flow unifier 1510 (which in turn may comprise a rod array), a mixing region 1520, and an outlet 1530 (preferably streamlined (SL)). These sections may be connected using threaded overlaps sealed using two o-rings for each connection. The DPI may be connected to the spacers using a threaded connection to match luer-lock style threads on the device outlets. All tubing connections may be sealed using a similar sealing system to the device, where the male connector is inserted (with two o-rings for sealing) into the corresponding female connector (either on the cannula or Y-connector) and twisted 30° to lock into place.

Total volume of the spacer airflow region is preferably small, e.g., 30-35 cm$^3$, which adds a small amount of travel time to the aerosol moving through the system. In a prototypical spacer, the total volume of the spacer that the aerosol traveled though was 33.7 cm$^3$. The straight mixing section had a diameter and length of 30 mm and 25 mm, respectively. The mixing section then smoothly connected to a 4 mm tubing outlet over a length of 55 mm.

The ventilation gas is passed through the flow unifier to generate a constant velocity gas stream that surrounds the inlet aerosol plume. This arrangement is configured to reduce wall deposition and minimize turbulence in the spacer. The flow unifier may comprise or consist of multiple rod arrays contained on disks with each disk rotated by 90 degrees forming a 3D mesh. Each rod array may comprise a plurality of equally spaced cylindrical rods which span the opening of the conduit. The streamlined outlet 1520 of the spacer 1500 may be located sufficiently far from the inlet to reduce impaction losses while maintaining a compact volume and small increase to travel time.

In some embodiments it is preferred that the aerosol be created in short bursts to enable synchronization with inhalation and maximize the probability of the aerosol entering the lungs. A short burst may be, for example, 1 sec in duration or less, 0.9 sec in duration or less, 0.8 sec in duration or less, 0.7 sec in duration or less, 0.6 sec in duration or less, 0.5 sec in duration or less, 0.4 sec in duration or less, 0.3 sec in duration or less, 0.2 sec in duration or less, or 0.1 sec in duration or less. Tests employing a 0.2 sec duration burst delivering 3 LPM flow rate proved effective. To remain unobtrusive, small diameter tubing and small nasal cannula bore sizes may be used, typically with internal diameters (IDs) in the range of 2-4 mm. Compared with jet and mesh nebulizers, advantages of inline DPIs include rapid dose delivery, the capability to quickly deliver high dose medications, reduced expense and stable drug formulations.

Where desired to ensure smooth interior surfaces, components of above-described devices and systems may be treated or manufactured to have certain surface properties. For instance, to ensure smooth interior surfaces, connectors and cannulas (and/or other components) may be manufactured using techniques such as stereolithography (SLA) and/or coated in low surface energy materials such as PTFE or anti-static materials. Some prototype devices discussed herein were built using stereolithography (SLA) in Accura ClearVue by 3D Systems On Demand Manufacturing (3D Systems Inc., Rock Hill, S.C.).

An additional benefit to exemplary systems is how quickly aerosol administration may be performed. Provided the low volume of dispersion air necessary to actuate the DPI and substantially empty the powder for the CU (e.g., 10 mL), the DPI actuation may be completed in a fraction of a second (e.g., 0.2 sec) and the delivery duration from the cannula (the duration of time that aerosol is existing the cannula) may be less than 3 seconds, preferably less than 2 seconds, more preferably less than 1 second. The LFNC ventilation gas may be delivered at a constant rate in the range of 5 to 8 LPM, for example. The additional volume of flow from the DPI, e.g. 10 mL, constitutes a brief fluctuation to the flow rate but does not necessarily require any adjustment to the LFNC ventilation stream flow rate. For example, a 10 mL pulse over 0.2 sec generates approximate 3 LPM flowrate for a 0.2 sec duration. The LFNC ventilation gas flow rate in turn may be only a fraction of total inspired air. For instance, a deep nasal inhalation by an adult human may be about 42 LPM. The low volume required by embodiments of the instant invention make it suitable for both low air volume and high air volume therapies.

EXAMPLES

Example 1. Effect of Powder Bed Location on Deaggregation

In some preferred embodiments of a containment unit dry powder inhaler, the powder bed is not in the path of the direct inlet airflow or inlet jet. FIGS. 10 and 11 illustrate two prototypical containment unit DPIs. Both devices were filled with 10 mg of a spray dried excipient enhanced growth powder formulation containing albuterol sulfate (AS—model drug), leucine, and mannitol. In both devices, 10 ml boluses of air were injected using a hand operated syringe creating a flow rate of approximately 3 L/min. In the orientation of intended use, the loaded powder forms a powder bed due to the action of gravity. In the straight through (ST) air flow path device shown in FIG. 10, the powder bed is not in the path of the inlet airflow. In contrast, with the single sided (SS) device, the inlet airflow is aimed directly at the powder bed. Based on inlet Reynolds number (6,758), the inlet air jet traverses a significant majority of the CU length (~90% or more). In this comparison, the inlet orifice diameter was 0.6 mm and the outlet orifice diameter was 1.17 mm for both devices. The inlet and outlets protruded into the containment unit volume by a distanced of 6 mm.

Methods

In vitro experiments were conducted to characterize the aerosolization performance of the ST and SS devices. To maintain a consistent distance from the outlet of the devices to the inlet of the Next Generation Impactor (NGI) for aerosol sizing, a custom adaptor was fabricated which held the DPIs approximately 3 cm away from the NGI preseparator inlet. The powders were aerosolized with the DPIs in the intended operation position relative to gravity. As minimal size change is expected in the aerosol under ambient temperature and relative humidity (RH) conditions, experiments were conducted with ambient air (T=22±3° C. and RH=50±5%) with the NGI at room temperature. The NGI was operated at 45 L/min and the preseparator and individual stages were coated with MOLYKOTE® 316 silicone spray (Dow Corning, Midland, Mich.) to minimize particle bounce and re-entrainment. The NGI flowrate of 45 L/min was chosen to ensure collection of the aerosol, which exited the device 3 cm away from the preseparator inlet, and maintain reasonable stage cutoff diameters for evaluating a small size aerosol. To actuate the DPI, the plunger of the syringe was depressed quickly (~0.2 seconds to empty) to aerosolize the powder into the inlet of the NGI. After aerosolization, drug masses retained in the containment unit, device, and the drug collected on the preseparator, impaction plates and the filter of the NGI were recovered by washing with appropriate volumes of deionized water and quantified by HPLC analysis. The mass of AS retained in the capsule and device, determined by HPLC, was expressed as a percentage of the loaded AS dose.

Results

For delivering aerosols using the excipient enhanced growth technique, or for nose-to-lung delivery or delivery to children, aerosol size should be below approximately 2 μm with fine particle fraction <5 μm based on emitted dose ($FPF_{<5\ \mu m}$) >90% and $FPF_{1\ \mu m}$ >20%. As shown in Table 2, the ST device (powder bed not in the direct inlet airflow path) achieves these metrics with an emitted MMAD of 1.64 μm. In contrast, the ST device (powder bed in the direct inlet airflow path) produced a much larger aerosol (3.12 μm) and did not meet any of the desired size metrics. As a result, it is shown that moving the powder out of the direct inlet airflow improves deaggregation and provides a desirable small aerosol size. The SS device aerosolizes the powder too quickly thereby increasing the chances that aggregates will form in the aerosol. In contrast, the ST approach aerosolizes the powder more gradually, reducing the chances for aggregates to reform and applying high shear and turbulent forces as the powder exits the containment unit.

TABLE 2

Aerosolization performance of ST (powder bed not in the path of the direct inlet airflow) vs.SS (powder bed in the path of the direct inlet airflow) DPI devices. Values are means (standard deviations), n ≥3 runs.

|  | FPF $_{<5\mu m}$ based on emitted dose (%) | FPF $_{<1\mu m}$ based on emitted dose (%) | MMAD (μm) |
| --- | --- | --- | --- |
| ST Device (FIG. 10) | 93.7 (1.3) | 23.8 (6.0) | 1.64 (0.09) |
| SS Device (FIG. 11) | 61.6 (8.9) | 9.6 (1.4) | 3.12 (0.40) |

Example 2. Effect of Outlet Diameter to Inlet Diameter Ratio on Performance

As illustrated in FIG. 9, a larger outlet diameter relative to the inlet diameter decelerates the inlet airflow and induces secondary velocities in the containment unit. These secondary velocities are used to aerosolize the powder bed. Some secondary velocity is desirable; however, too much may aerosolize the powder too quickly and start to increase particle size.

Methods

Devices were constructed using the straight-through design shown in FIG. 10 with outlet/inlet orifice diameter ratios of 0.6/0.6 mm, 0.89/0.6 mm, and 1.17/0.6 mm. All devices had an inlet Reynolds number of 6,758. Each device was filled with 10 mg of spray dried excipient enhanced growth aerosol formulation containing albuterol sulfate (AS), mannitol, and leucine. The devices were actuated five times with 10 ml of air delivered from a hand operated syringe. Aerosol size was calculated based on cascade impaction with an NGI and HPLC analysis using a validated method. The emitted dose was calculated by subtracting the mass of AS retained in the device from the loaded AS dose.

Results

Results are presented in Table 3. As observed in the table, increasing the outlet diameter from 0.6 to 0.89 mm for the same inlet diameter increases emitted dose from 44.8 to 63.1%. This increase is likely because of increased secondary velocities due to the inlet vs. outlet diameter mismatch. However, there is a limit to this relationship. As the outlet becomes larger, the aerosol may be formed too quickly allowing aggregates to form in the flow stream. This is observed when going from the 0.89 mm to 1.17 mm outlet. Statistically the emitted doses between these cases are similar. However, the aerosol size increases from 1.56 μm with the 0.89 mm outlet to 1.64 μm with the 1.17 mm outlet. As a result, an exemplary outlet to inlet diameter ratio may be >1 and <2, and preferably approximately 1.5. Outlet to inlet ratios in the range of 2.0 and above may be too large to effectively aerosol the powder with secondary velocities.

TABLE 3

Aerosolization performance of ST (powder bed not in the path of the direct inlet airflow) DPI device with different outlet to inlet orifice diameter ratios. Orifices protrude 6 mm into the containment unit volume. Values are means (standard deviations), n ≥3 runs.

| Outlet to inlet ratio | Emitted dose (% of loaded dose) | MMAD (μm) |
| --- | --- | --- |
| 0.6/0.6 mm | 44.8 (4.8) | 1.57 (0.04) |
| 0.89/0.6 mm | 63.1 (4.8) | 1.56 (0.01) |
| 1.17/0.6 mm | 57.3 (4.9) | 1.64 (0.09) |

Example 3. Correlations Predicting Performance of the Containment Unit DPI

It is widely held that turbulent kinetic energy, which quantifies the energy of turbulent fluctuations, works to deaggregate an aerosol and reduce aerosol size.

Methods

In this example, computational fluid dynamics (CFD) was used to predict the turbulent characteristics of five containment unit DPIs with inlet and outlet orifices diameters in the range of 0.6 mm to 1.17 mm. The related inlet Reynolds number range was 3,465 to 6,758. All DPIs had a straight through design as shown in FIG. 10 with the powder not in the path of the direct inlet airflow. The DPIs were actuated with air bursts of 3 LPM. CFD calculation including turbulent, transient and compressible flow effects were used to calculate the volume-averaged turbulent kinetic energy (k) of the three dimensional field within the dose containment DPI with k express in $m^2/s^2$. The turbulent kinetic energy values were made non-dimensional (ND) by dividing by the inlet velocity raised to the $2^{nd}$ power in each case resulting in the parameter $k_{field}$ND. Corresponding in vitro experiments with cascade impaction were conducted to measure the aerosol size in terms of mass median aerodynamic diameter (MMAD) for each device.

Results

Figure 16:
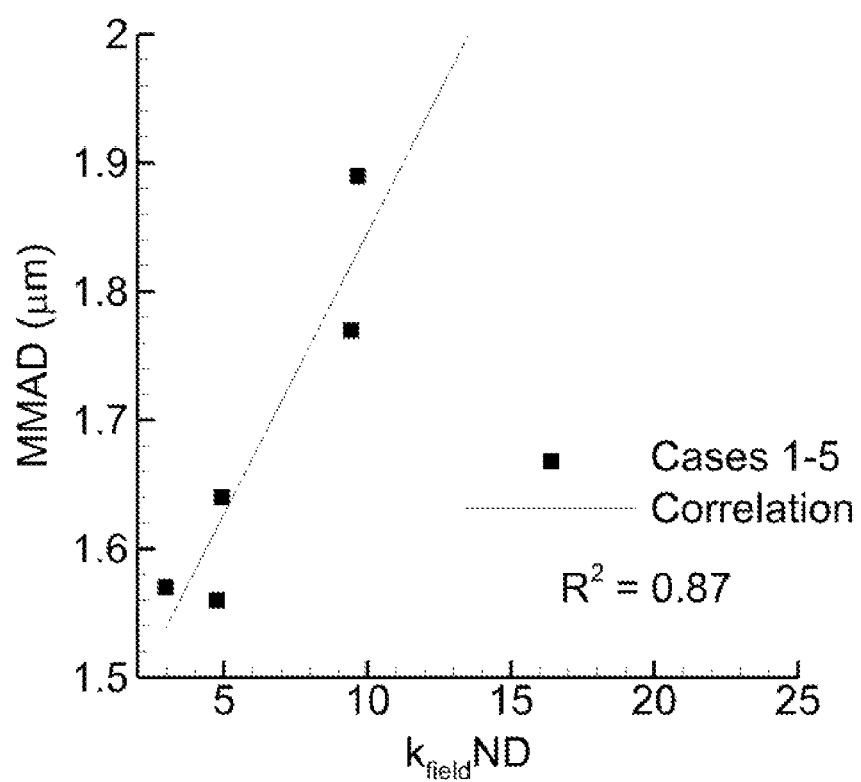
FIG. 16. Non-dimensional values of turbulent kinetic energy (k) vs. experimentally measured aerosol size as a mass median aerodynamic diameter (MMAD). The direct relationship indicates that forming the aerosol too quickly, as occurs with elevated values of k, can create aerosol aggregation and an undesirable increase in aerosol size.

FIG. 16 plots the relationship between the $k_{field}$ND and the experimentally measured MMAD. Surprisingly, increasing $k_{field}$ND in the system increases the MMAD. Typically, increasing turbulent kinetic energy is expected to deaggregate the aerosol and decrease the MMAD. The best explanation is that with increasing turbulent kinetic energy, the aerosol is formed more rapidly due to the increased velocity fluctuations such that aerosol aggregates form within the airstream and increase the emitted aerosol size. This example provides evidence that forming the aerosol too quickly can have the detrimental effect of increasing the final aerosol size. To slow the rate of aerosol production, the $k_{field}$ND should remain within specific limits. The rate of aerosol production can also be slowed by removing the powder bed from the direct inlet airflow path as shown in other case studies.

Example 4. High Efficiency Aerosol Delivery Through a Challenging Low Flow Nasal Cannula System Low flow nasal cannula oxygen is a common form of respiratory support to treat patients with hypoxemia. This form of therapy delivers oxygen to the nasal cavity at gas flow rates up to ~8 LPM in adults and ~1 LPM in children. Patients receiving LFNC therapy and other forms of non-invasive ventilation often require pharmaceutical aerosols for the treatment of underlying lung conditions. Simultaneous administration of a pharmaceutical aerosol through noninvasive ventilation systems and into the lungs (nose-to-lung or N2L delivery) is viewed as convenient and prevents the removal of ventilator support during aerosol delivery. However, aerosol delivery efficiency through small diameter tubing and cannula systems is known to be very low, with typical values in the range of 0.6-2.5% even at flow rates of 2-5 L/min.

Methods

As shown in FIG. 14, the experimental setup consisted of a syringe filled with room condition air, the containment unit DPI device, spacer, medical grade air (ventilation gas), small diameter Tygon tubing (4 mm ID), streamlined (SL) Y-connector, SL nasal cannula, realistic geometric nose-mouth-throat (NMT) model and artificial lung simulator (ASL 5000, IngMar Medical, Pittsburgh, Pa.) or vacuum pump. As with LFNC therapy, ventilation gas was delivered at a constant flowrate, which in this example was 8 LPM. The nasal cannula was positioned in the nose with a gap between the nasal prongs and nostril to allow for patient exhalation. A downstream vacuum pump or the ASL was used to create steady state inhalation or cyclic breathing conditions, respectively. To deliver the aerosol, the syringe with 10 mL of room air was actuated by hand as rapidly as possible. High speed video indicated that actuation occurs in approximately 0.2 s with minimal resistance felt at the air syringe. Actuating the air syringe delivers a bolus of air at approximately 3 LPM through the inline containment unit DPI.

The containment unit DPI had a straight-through (ST) design as shown in FIG. 10 with an inlet orifice of 0.6 mm and an outlet orifice of 0.89 mm. The inlet Reynolds number was 6,758. The orifices protruded into the containment unit by approximately 2 mm. The DPI was operated in the horizontal position with respect to gravity as shown in FIG. 10.

A custom spacer as shown in FIG. 15 was used to combine the intermittent aerosol stream with the continuous LFNC gas stream. The spacer included an inlet flow unifier (containing a rod array), mixing region and streamlined outlet. Total volume of the spacer airflow region is 33.7 cm$^3$, which adds a small amount of travel time to the aerosol moving through the system. The ventilation gas is passed through the flow unifier to generate a constant velocity gas stream that surrounds the inlet aerosol plume. This arrangement is configured to reduce wall deposition and minimize turbulence in the spacer. The flow unifier consists of multiple rod arrays contained on disks with each disk rotated by 90 degrees forming a 3D mesh.

The streamlined outlet of the spacer is located sufficiently far from the inlet to reduce impaction losses while maintaining a compact volume and small increase to travel time.

The airway geometry consists of a nose-mouth-throat (NMT) in vitro model that extends from the nostrils through the larynx. This geometry was extracted from CT scans of adult human subjects and created using 3D printing.

Both steady state inhalation airflow at 42 L/min and cyclic breathing conditions were generated in the in vitro nasal model using a vacuum pump or an artificial lung simulator, respectively. For cyclic ventilation, passive nasal breathing was considered with an inhalation time of 1.7 s, a mean flow rate of 27 L/min and a maximum flow rate of 42.3 L/min. Deep nasal breathing was also considered with an inhalation time of 2.5 s, a mean flow rate of 42 L/min and a maximum flow rate of 66 L/min.

Aerosolization performance was assessed using 10 mg powder masses of a spray dried excipient enhanced growth (EEG) formulation containing albuterol sulfate (AS), mannitol and leucine. The containment unit DPI was actuated five times with 10 ml boluses of air delivered quickly (~0.2 s) using a hand operated syringe. For experiments using cyclic breathing, the air syringe was actuated at the beginning of inhalation.

After aerosolization, drug masses retained in the capsule, device, spacer, system components (tubing, Y-connector and cannula), NMT model and tracheal filter were recovered by washing with appropriate volumes of deionized water and quantified by HPLC analysis. The mass of AS retained or deposited in each component was expressed as a percentage of the AS dose loaded into each capsule. In order to determine the nominal dose of AS in the EEG-AS formulation, known masses of the formulation were dissolved in 50 mL of water and the mean amount of AS per mg of formulation was determined using HPLC analysis. For each aerosolization experiment, the measured formulation AS content and the mass of formulation loaded into the capsule was used to determine the loaded dose of AS.

Results

For an optimized system including the containment unit DPI, spacer, streamlined y-connector and streamlined cannula, aerosol delivery performance is shown in Table 4. The tracheal filter dose is assumed to approach the total lung dose that would be received by a living subject. As shown in the table, the cannula emitted dose is approximately 70% even with cyclic nasal breathing. This value is significantly higher than with previous studies where 0.6-2.5% of the dose exits the cannula at similar flow rates of 2-5 L/min. Due to the small aerosol size arising from efficient aerosolization, the depositional loss in the NMT region is low. The resulting lung delivered dose (filter deposition) is greater than 50% of the loaded dose. These values are also significantly higher than recent human subject studies with nose-to-lung delivery using a nasal cannula interface, where for example Dugernier et al. reported 1-3.6% of the nebulized dose reached the subjects lungs (Dugernier J, et al. Aerosol delivery with two nebulizers through high-flow nasal cannula: A randomized cross-over single-photon emission computed tomography study. Journal of Aerosol Medicine and Pulmonary Drug Delivery 2017; 30:349-358).

For comparison, Table 5 illustrates tracheal filter delivery using the same experimental setup, NMT model and passive nasal breathing but with a commercial mesh nebulizer (Aeroneb Solo device) and commercial components for LFNC administration. With the commercial system, the tracheal filter dose was only 1.4% of the aerosolized dose of drug. Therefore, the containment unit DPI improved lung delivery efficiency compared with the commercial system by a factor of approximately 40-fold using the same NMT model and passive nasal breathing conditions.

TABLE 4

Recovery of drug for ST (powder bed not in the path of the direct inlet airflow) containment unit DPI device when administering aerosol during low flow nasal cannula therapy. Values are means (standard deviations), n ≥3 runs.

| Description | Steady State | Deep Nasal | Passive Nasal |
|---|---|---|---|
| Capsule (%) | 8.6 (0.5) | 11.1 (2.6) | 9.5 (2.5) |
| Device (%) | 1.6 (0.4) | 1.7 (0.4) | 1.7 (0.6) |
| Device ED (%) | 89.8 (0.2) | 87.2 (2.9) | 88.8 (2.9) |
| Spacer (%) | 6.4 (0.8) | 7.4 (2.2) | 7.3 (1.6) |
| Y Retention (%) | 0.5 (0.1) | 0.7 (0.3) | 0.7 (0.3) |
| Tubing Retention (%) | 4.0 (0.8) | 5.0 (1.8) | 4.9 (1.4) |
| Cannula Retention (%) | 4.1 (1.2) | 4.7 (1.9) | 4.6 (1.5) |

TABLE 4-continued

Recovery of drug for ST (powder bed not in the path of the direct inlet airflow) containment unit DPI device when administering aerosol during low flow nasal cannula therapy. Values are means (standard deviations), n ≥3 runs.

| Description | Steady State | Deep Nasal | Passive Nasal |
|---|---|---|---|
| Cannula ED (%) | 74.7 (3.0) | 69.3 (4.2) | 71.4 (1.9) |
| NMT (%) | 6.9 (2.0) | 8.9 (3.1) | 6.2 (2.1) |
| Tracheal Filter (%) | 61.6 (4.8) | 53.4 (6.2) | 55.3 (4.1) |

*p <0.05 significant effect of system design on Recovery (one-way ANOVA).
**p <0.05 significant difference compared to Steady State (post-hoc Tukey).

TABLE 5

Aerosol delivery with the Aerogen Solo nebulizer using passive nasal inhalation conditions and 8 LPM system flow rate. Values represent aerosol deposition fractions as percentages of the nebulized dose and are means (standard deviations), n ≥3 runs.

| Description | Passive Nasal |
|---|---|
| Device (%) | 1.7 (0.9) |
| Tee (%) | 52.6 (3.3) |
| Tubing (%) | 29.9 (0.2) |
| Cannula ED (%) | 15.7 (3.8) |
| NMT (%) | 0.0 (0.0) |
| Tracheal Filter (%) | 1.4 (0.2) |

Example 5. Device Operation with a 3 ml Dispersion Air Volume

Methods The aerosol performance of a surfactant-EEG powder was determined following a series of design changes made to the straight-through DPI with a dose containment unit (DCU) volume of 0.21 mL. The Dv50 values and emitted masses for each iteration were determined and compared. For each comparison, powder was filled into the device, assembled and deaggregated using 3 mL pulses of dispersion air volume introduced into the device with a 5 mL disposable syringe attached to the luer lock inlet of the device. The delivery time for each 3 mL actuation of air was 0.12±0.01 sec, resulting in a delivery flow rate of 1.5 L/min. The particle size distribution of the aerosol exiting the device was determined by laser diffraction. The powder mass exiting the DPI was determined by weighing the assembled device with powder before and after each actuation using an analytical balance. The percent of powder mass emitted was calculated using the following equation:

$$\% \text{ emitted mass} = \frac{\text{mass of loaded device} - \text{mass of device after actuation}}{\text{initial powder fill mass}} \times 100$$

Effect of Number of Air Inlet Holes

Table 6 shows the aerosol characteristics of the containment unit DPI with one- and three-0.60 mm air inlet holes, both with outlet diameters of 0.89 mm. After the first actuation, the three-air inlet device demonstrated a significantly higher emitted mass with similar dispersion performance, Dv50 values of 2.7 μm, compared to the one-air inlet device at a 3 mg fill mass. Similar percent particle fractions were observed for both devices and >80% of the fill mass was emitted following three-3 mL actuations of air for both devices.

TABLE 6

Effect of number of air inlet holes (one-0.60 mm hole vs. three-0.60 mm holes) on aerosol characteristics using 3 mL dispersion air volume to deliver 3 mg fill mass. Values are means (standard deviations), n ≥3 runs.

| | $1^{st}$ actuation | | | | |
|---|---|---|---|---|---|
| Device | Mass emitted, % nominal | Dv50, μm | particle fraction <1 μm, % | particle fraction <5 μm, % | Cumulative mass emitted after $3^{rd}$ actuation, % nominal |
| One air inlet | 55.5 (5.7) | 2.7 (0.6) | 23.3 (3.4) | 62.5 (10.5) | 83.1 (7.9) |
| Three air inlets | 70.9 (3.7) | 2.7 (0.4) | 26.9 (2.1) | 57.5 (2.6) | 92.4 (1.9) |

Effect of Outlet Diameter ($d_{outlet}$)

The effect of outlet diameter ($d_{outlet}$) on emitted mass and Dv50 values were studied using the containment unit DPI with three-air inlet holes and a 3 mg fill mass (Table 7). Decreasing the $d_{outlet}$ from 0.89 mm to 0.60 mm resulted in better powder dispersion (2.7 to 1.7 μm, respectively), but significantly reduced the emitted mass on the first actuation. The smaller $d_{outlet}$ resulted in higher percent particle fractions, but a lower cumulative emitted mass after three actuations compared to the device with a $d_{outlet}$ of 0.89 mm. Increasing the $d_{outlet}$ from 0.89 mm to 1.17 mm resulted in a higher, although not significantly higher, emitted mass on the first actuation, but with poorer powder dispersion (2.7 to 6.8 μm, respectively). The increased outlet diameter resulted in decreased percent particle fractions, but with better overall emptying after three actuations compared to the device with a $d_{outlet}$ of 0.89 mm.

TABLE 7

Effect of outlet diameter ($d_{outlet}$) on aerosol characteristics using 3 mL dispersion air volume to deliver 3 mg fill mass. Values are means (standard deviations), n = 3.

| | $1^{st}$ actuation | | | | |
|---|---|---|---|---|---|
| $d_{outlet}$, mm | Mass emitted, % nominal | Dv50, μm | particle fraction <1 μm, % | particle fraction <5 μm, % | Cumulative mass emitted after $3^{rd}$ actuation, % nominal |
| 0.60 | 33.9 (0.3) | 1.7 (0.1) | 32.6 (0.2) | 73.5 (5.7) | 70.8 (2.6) |
| 0.89 | 70.9 (3.7) | 2.7 (0.4) | 26.9 (2.1) | 57.5 (2.6) | 92.4 (1.9) |
| 1.17 | 74.2 (4.7) | 6.8 (0.1) | 12.0 (1.1) | 44.7 (0.7) | 98.2 (3.6) |

Effect of Outlet Length

At a 5 mg fill mass, the effect of outlet length was studied for the three-air inlet hole device with a $d_{outlet}$ of 0.89 mm (Table 8). The emitted masses on the first actuation were similar across all outlet lengths except at the shortest length of 7 mm, which had the highest emitted mass of 68% of nominal. The cumulative mass emitted after three actuations were >72% for all outlet lengths. Correlations of DPI outlet length were observed with Dv50 values and percent particle fractions:

$$Dv50(\mu m) = 15.48 - 0.1604 * \text{outlet length}, R^2 = 0.7706,$$

$$\text{Particle fraction} < 1 \ \mu m \ (\%) = 7.861 + 0.2410 * \text{outlet length}, R^2 = 0.8631,$$

$$\text{Particle fraction} < 5 \ \mu m \ (\%) = 26.984 + 0.3547 * \text{outlet length}, R^2 = 0.7863.$$

TABLE 8

Effect of outlet length on aerosol characteristics using 3 mL dispersion air volume to deliver 5 mg fill mass. Values are means (standard deviations), n = 3.

| | 1st actuation | | | | |
|---|---|---|---|---|---|
| Outlet length, mm | Mass emitted, % nominal | Dv50, μm | particle fraction <1 μm, % | particle fraction <5 μm, % | Cumulative mass emitted after 3rd actuation, % nominal |
| 90 | 56.2 (4.4) | 2.7 (0.2) | 29.3 (1.2) | 55.0 (0.7) | 94.8 (3.1) |
| 55 | 54.9 (4.2) | 3.2 (0.3) | 24.5 (1.8) | 54.7 (1.1) | 87.8 (2.7) |
| 45 | 56.7 (2.5) | 7.2 (1.8) | 15.2 (1.3) | 44.5 (3.7) | 76.5 (0.8) |
| 30 | 54.1 (0.6) | 13.5 (1.7) | 14.8 (3.1) | 32.1 (2.5) | 72.4 (3.7) |
| 7 | 68.1 (6.4) | 14.3 (1.0) | 10.2 (0.7) | 29.2 (1.0) | 88.0 (5.7) |

Effect of Fill Mass

The effect of fill mass was determined for the 90 and 45 mm outlet length devices with three-air inlet holes and a $d_{outlet}$ of 0.89 mm (Table 9). The 3 mg fill mass for both outlet lengths had significantly higher emitted masses on the first actuation compared to the 5 and 10 mg fill masses. For the 90 mm outlet length device, dispersion was observed to be independent of fill mass (Dv50 of 2.7 μm across all fill masses), whereas dispersion worsened with increasing fill mass in the 45 mm device. The percent particle fractions were less variable across fill masses for the 90 mm device, while the percent particle fractions for the 45 mm device appeared dependent on fill mass showing decreasing particle fractions with increasing fill mass.

TABLE 9

Effect of fill mass on aerosol characteristics with the 90 mm and 45 mm outlet length devices using 3 mL dispersion air volume. Values are means (standard deviations), n = 3.

| | 1st actuation | | | | |
|---|---|---|---|---|---|
| Fill mass, mg | Mass emitted, % nominal | Dv50, μm | particle fraction <1 μm, % | particle fraction <5 μm, % | Cumulative mass emitted after 3rd actuation, % nominal |
| 90 mm outlet length | | | | | |
| 3 | 70.9 (3.7) | 2.7 (0.4) | 26.9 (2.1) | 57.5 (2.6) | 92.4 (1.9) |
| 5 | 56.2 (4.4) | 2.7 (0.2) | 29.3 (1.2) | 55.0 (0.7) | 94.8 (3.1) |
| 10 | 52.3 (4.4) | 2.7 (0.2) | 24.6 (1.2) | 61.8 (2.2) | 85.4 (3.0) |
| 45 mm outlet length | | | | | |
| 3 | 66.8 (4.4) | 2.7 (0.6) | 21.4 (4.3) | 65.3 (13.5) | 88.3 (3.5) |
| 5 | 56.7 (2.5) | 7.2 (1.8) | 15.2 (1.3) | 44.5 (3.7) | 76.5 (0.8) |
| 10 | 54.7 (6.2) | 9.1 (0.7) | 13.4 (0.2) | 39.8 (1.4) | 79.8 (6.1) |

Example 6. Application in a Higher Flow Device

The CU may also be implemented in a higher flow device intended for direct oral inhalation and operated either with negative inhalation pressure (as with a passive DPI) or a positive pressure ventilation bag. A pediatric delivery scenario was developed in which a 5-year-old in vitro subject inhaled 750 ml of air and the inhaler was assisted by a positive pressure ventilation bag delivering 6000 Pa of pressure at the inhaler inlet. To enable use with higher flow rates, inlet and outlet orifice diameters were 2.4 mm, and protruded approximately 4 mm into the 0.68 ml CU. The device used the ST design and was operated in the horizontal position. The aerosol formulation was 10 mg of tobramycin excipient enhanced growth powder spray dried with leucine and mannitol. Aerosol characterization was similar to the methods used in Example 1. In separate experiments, flow through the device driven by the positive upstream pressure was measured.

Results

The measured flow rate through the device was approximately 15 L/min resulting in a 3 second actuation to deliver the desired 750 ml of gas flow, which is consistent with typical inhaler usage. The resulting Reynolds number was 8,447. Device emitted dose was 93.7% of the loaded dose and the aerosol MMAD was 2.1 μm based on cascade impaction. At an inhalation flow rate of 15 L/min, mouth-throat depositional loss is expected to be very low (<10% of the emitted dose). Modifications described for the CU device may be implemented to further reduce initial particle size below 2.0 μm if desired.

While exemplary embodiments of the present invention have been disclosed herein, one skilled in the art will recognize that various changes and modifications may be made without departing from the scope of the invention as defined by the following claims.

We claim:

1. A containment unit for a dry powder inhaler (DPI), comprising one or more containing walls which enclose and protect a dry powder from external conditions, wherein the dry powder is or contains a medicament for oral inhalation or nasal administration; at least one inlet that defines an inlet orifice in the one or more containing walls that has a fixed geometry which does not change from use of the containment unit; at least one outlet that defines an outlet orifice in the one or more containing walls that has a fixed geometry which does not change from use of the containment unit, wherein the inlet and outlet orifices are spaced apart; and an interior space within the one or more containing walls that permits the dry powder to form a powder beds wherein the fixed geometry of the inlet orifice is configured to form an inlet air jet along a straight geometric line, wherein the powder bed lies outside the straight geometric line when the containment unit is in an orientation of use, and wherein a direct linear path exists between the at least one inlet and the at least one outlet.

2. The containment unit of claim 1, wherein the inlet and outlet orifices are sized to produce secondary flows within the containment unit.

3. The containment unit of claim 2, wherein the inlet orifice is smaller than the outlet orifice.

4. The containment unit of claim 3, wherein a diameter of the inlet orifice is smaller than a diameter of the outlet orifice.

5. The containment unit of claim 3, wherein a cross sectional area of all inlet orifices is smaller than the cross sectional area of all outlet orifices.

6. The containment unit of claim 1, wherein the containment unit has a geometric length, wherein the inlet air jet has a Reynolds number>100 for a majority of the geometric length.

7. The containment unit of claim 1, wherein the at least one inlet comprises an inlet protrusion from one of the one or more containing walls, and wherein the inlet orifice is at an end of the inlet protrusion.

8. The containment unit of claim 7, wherein the at least one outlet comprises an outlet protrusion from one of the one or more containing walls, and wherein the outlet orifice is at an end of the outlet protrusion.

9. A dry powder inhaler (DPI) device, comprising one or more DPI containment units (CUs) as recited in claim 1; and an inhaler configured to receive one of the CUs and position the CU in the orientation of use whereby the powder bed lies outside the straight geometric line.

10. The DPI device of claim 9, wherein the inhaler is further configured to position the CU in-line with a flow path of the inhaler.

11. The DPI device of claim 9, wherein the inhaler is configured as a passive oral inhaler operable by subject inhalation force.

12. The DPI device of claim 9, further comprising a positive pressure air source.

13. The DPI device of claim 9, further comprising a nasal cannula interface, nasal mask, oral mask, and oral-nasal mask, endotracheal tube, or a mouthpiece.

14. The DPI device of claim 9, wherein the orientation of use orients the straight geometric line horizontally.

15. The DPI device of claim 9, wherein the orientation of use orients the straight geometric line vertically.

16. A dry powder inhaler (DPI) delivery system, comprising one or more DPI containment units (CU) as recited in claim 1;

an inhaler configured to contain the one or more CUs and position each CU at a time of use in the orientation of use whereby the powder bed lies outside the straight geometric line; and a mixing region configured to combine an aerosol stream from the inhaler with a ventilation gas stream prior to the aerosol stream exiting the DPI delivery system.

17. The DPI delivery system of claim 16, further comprising an inlet flow unifier and a streamlined outlet.

18. The DPI delivery system of claim 16, wherein the inhaler is actuatable in bursts synchronized with subject inhalation cycles.

19. The DPI delivery system of claim 18, wherein the ventilation gas stream is operated continuously.

20. The DPI delivery system of claim 16, wherein the ventilation gas stream is a low flow nasal cannula (LFNC) or high flow nasal cannula (HFNC) stream.

21. The containment unit of claim 1, wherein the interior space is a cylindrical cavity or an elliptical shape.

22. The containment unit of claim 21, wherein the straight geometric line is a center longitudinal axis of the cylindrical cavity or elliptical shape.

23. The containment unit of claim 1, wherein the inlets and outlets are a different material than the one or more containing walls.

24. The containment unit of claim 1, wherein the one or more containing walls comprise smooth curved surfaces that connect the inlet with a remainder of the one or more containing walls.

25. The containment unit of claim 1, wherein the one or more containing walls include curved surfaces to either side of the at least one inlet.

26. The containment unit of claim 1, wherein the interior space includes space both above and below the inlet orifice.

27. The containment unit of claim 1, wherein the inlet orifice has a circular cross section.

28. The containment unit of claim 1, wherein the straight geometric line intersects with one of the one or more containing walls, and wherein secondary flows are produced within the containment unit from the straight geometric line which does not intersect the powder bed.

29. A dry powder inhaler (DPI), comprising at least one containment unit (CU) comprising one or more containing walls which enclose and protect a dry powder from external conditions, wherein the dry powder is or contains a medicament for oral inhalation or nasal administration; at least one inlet for making an inlet orifice in the one or more containing walls; at least one outlet for making an outlet orifice in the one or more containing walls; and an interior space within the one or more containing walls that permits the dry powder to form a powder bed, wherein the interior space is a cylindrical cavity or an elliptical shape, wherein during a state of use, the powder bed lies outside a straight geometric line coaxial with a center axis of the at least one inlet, wherein the straight geometric line is coaxial with a center axis of the at least one outlet, and wherein the one or more containing walls include curved surfaces to either side of the at least one inlet.

30. The DPI of claim 29, further comprising a body that is different from the at least one CU, wherein the body is separable into parts to load the at least one CU, wherein the parts are rejoinable after insertion of the at least one CU.

31. The DPI of claim 30, wherein the at least one CU is hermetically sealed prior to loading into the body, wherein loading of the at least one CU automatically opens the at least one CU.

32. The DPI of claim 29, wherein the at least one inlet consists of multiple inlets.

33. The DPI of claim 32, wherein the multiple inlets comprise three inlets the center axes of which do not intersect the powder bed.

34. The DPI of claim 32, wherein the multiple inlets comprise inlets the center axes of which do not intersect the powder bed.

* * * * *